United States Patent [19]

Kudo

[11] Patent Number: 5,402,461
[45] Date of Patent: Mar. 28, 1995

[54] X-RAY COMPUTED TOMOGRAPHY APPARATUS

[75] Inventor: Hidetoshi Kudo, Tochigi, Japan

[73] Assignee: Kabushiki Kaisha Toshiba, Kawasaki, Japan

[21] Appl. No.: 107,607

[22] Filed: Aug. 18, 1993

[30] Foreign Application Priority Data

Aug. 21, 1992 [JP] Japan ................ 4-222838

[51] Int. Cl.⁶ ............................. A61B 6/00
[52] U.S. Cl. ........................ 378/15; 378/111; 378/117
[58] Field of Search ........... 378/15, 4, 91, 101, 378/111, 117, 114; 310/228, 232, 248

[56] References Cited

U.S. PATENT DOCUMENTS

| | | | |
|---|---|---|---|
| 4,192,997 | 3/1980 | Baumann | 378/15 |
| 4,277,708 | 7/1981 | McNab et al. | 310/228 |
| 4,991,193 | 2/1991 | Cecil et al. | 378/117 |
| 5,018,174 | 5/1991 | Collins | 378/15 X |
| 5,208,581 | 5/1993 | Collins | 378/15 X |

FOREIGN PATENT DOCUMENTS 59-75161  4/1984  Japan .
1-177873  7/1989  Japan .

*Primary Examiner*—David P. Porta
*Attorney, Agent, or Firm*—Finnegan, Henderson, Farabow, Garrett & Dunner

[57] ABSTRACT

An X-ray computed tomography apparatus includes a rotating frame section, an X-ray generating system mounted on the rotating frame section, electric power transmission means constituted by a slip ring and a brush and designed to supply electric power to the X-ray generating system, and a detection means for detecting an electric power supply state in the electric power transmission means.

16 Claims, 6 Drawing Sheets

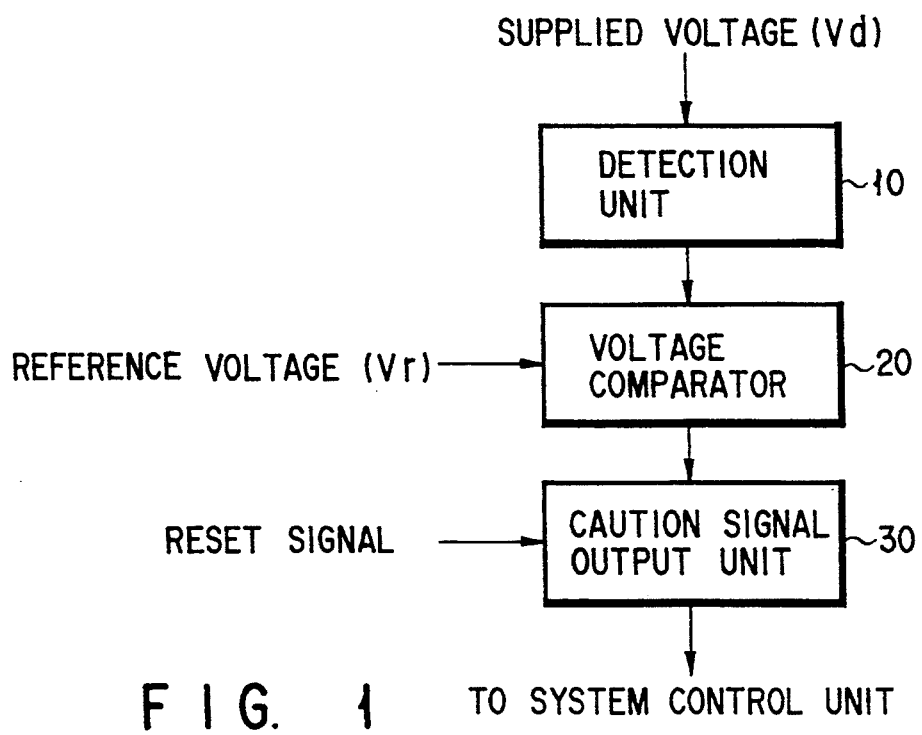
F I G. 1
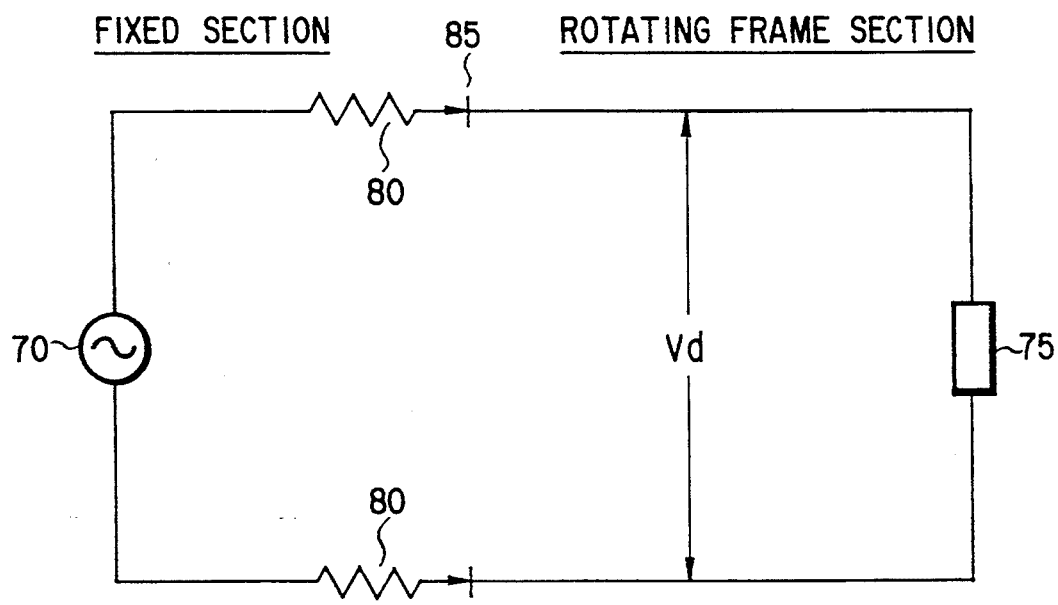
F I G. 2

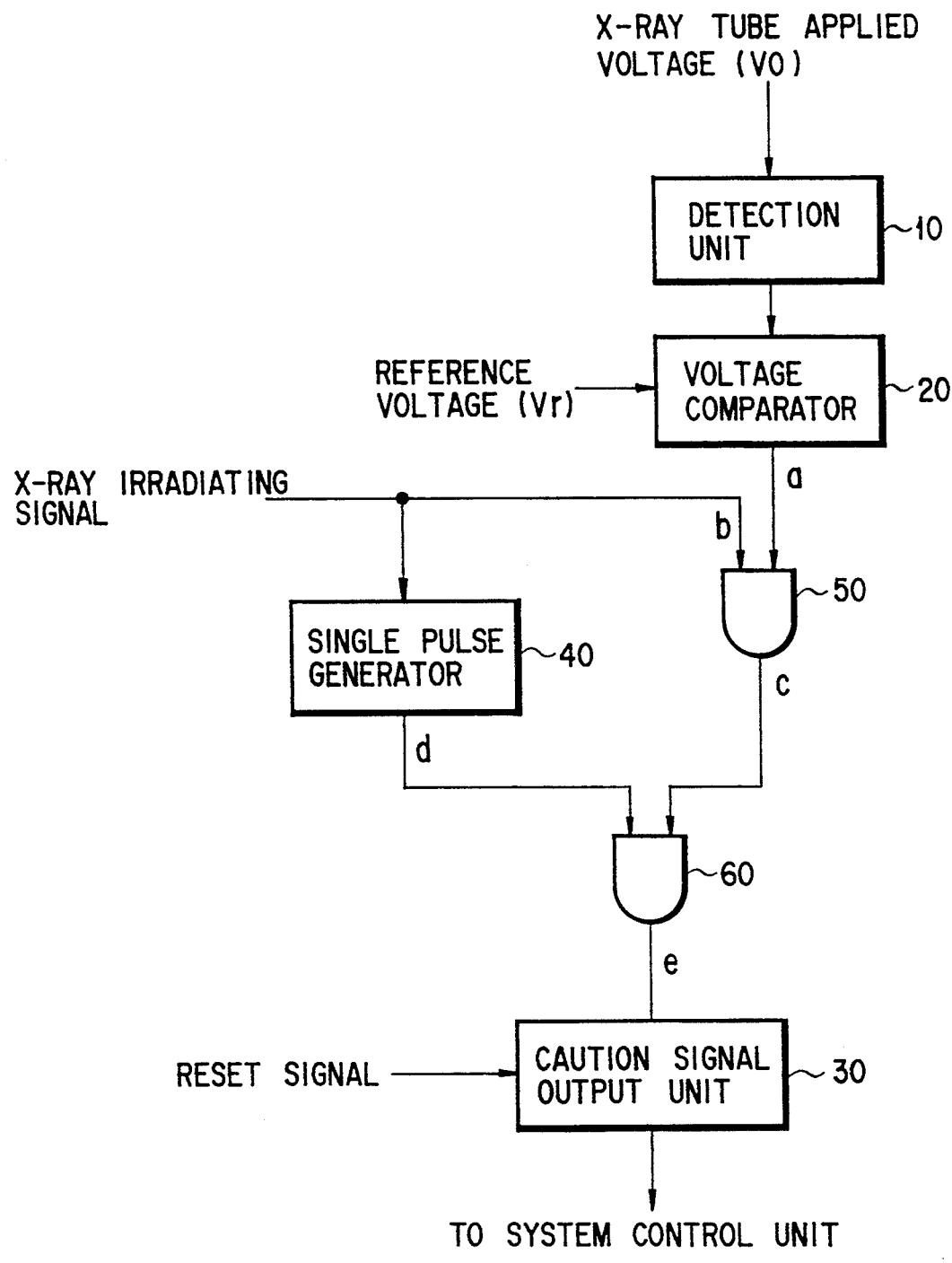
F I G. 3

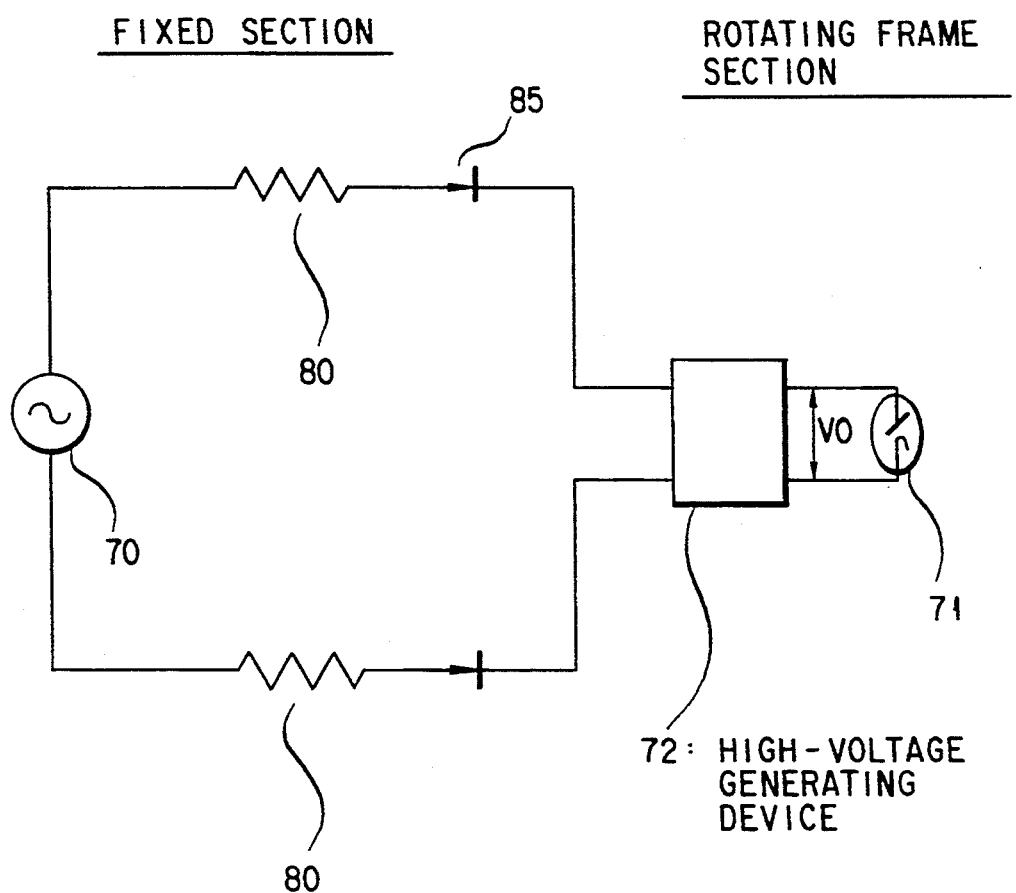
F I G. 4

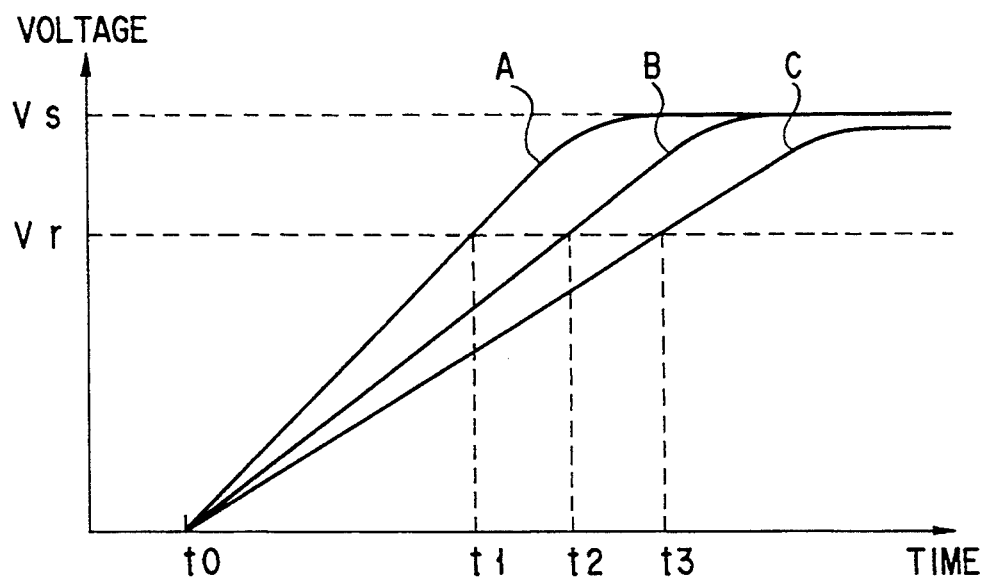
F I G. 5A
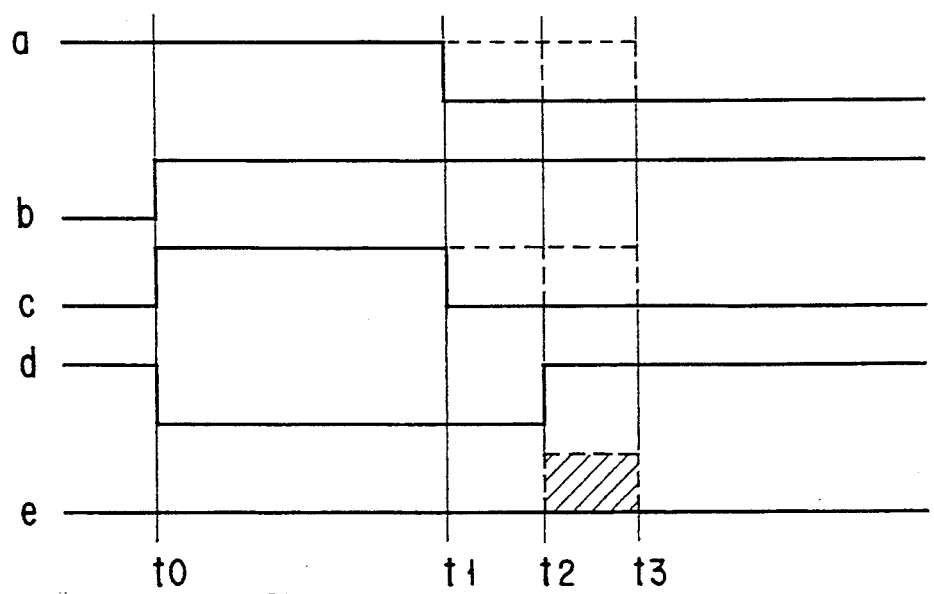
F I G. 5B

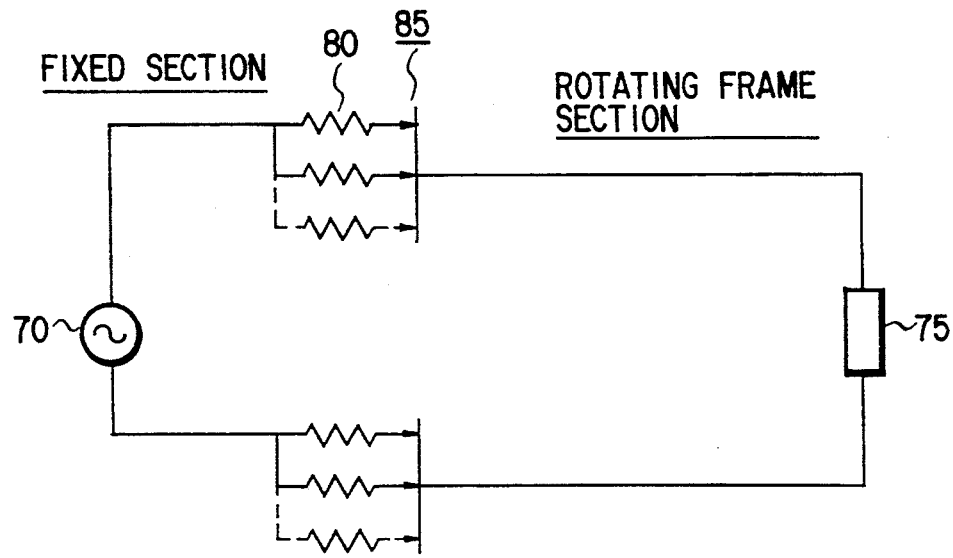
F I G. 6A
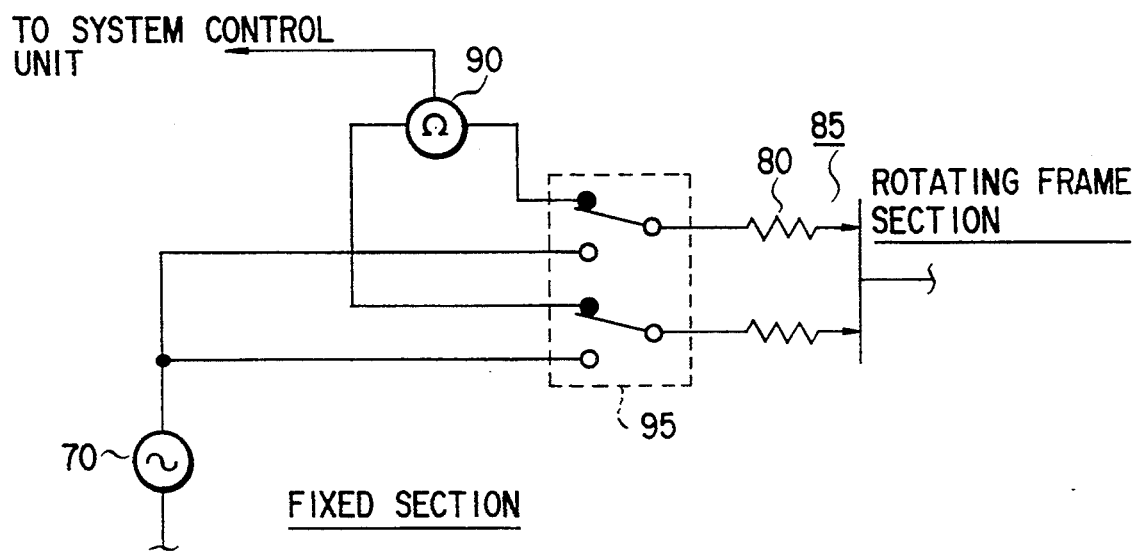
F I G. 6B

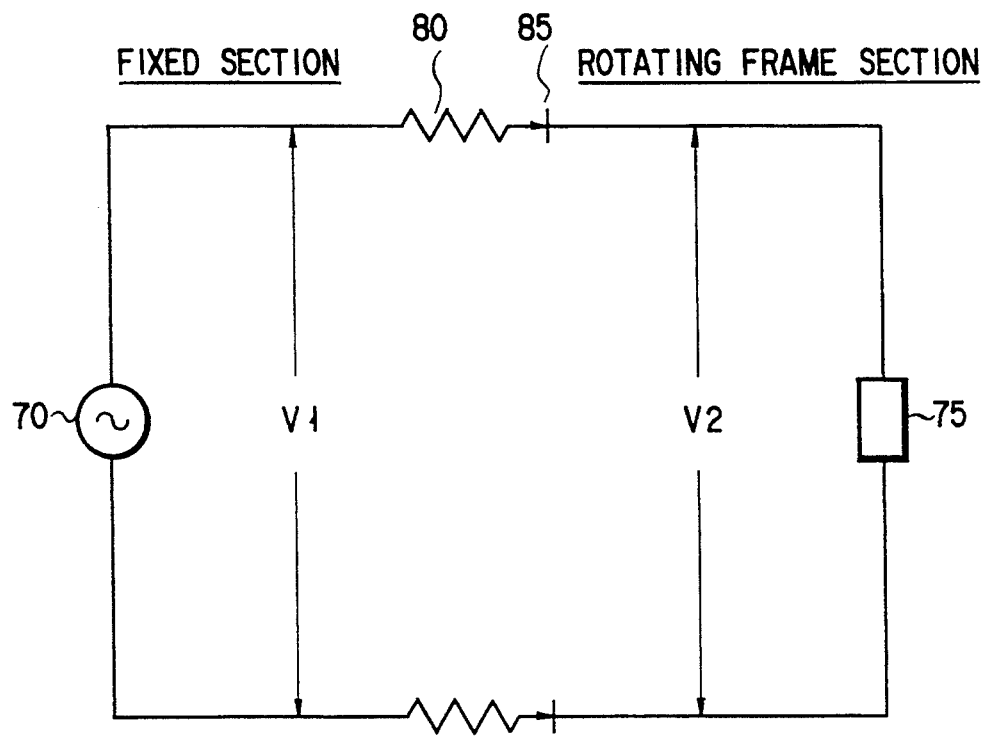
F I G. 7A
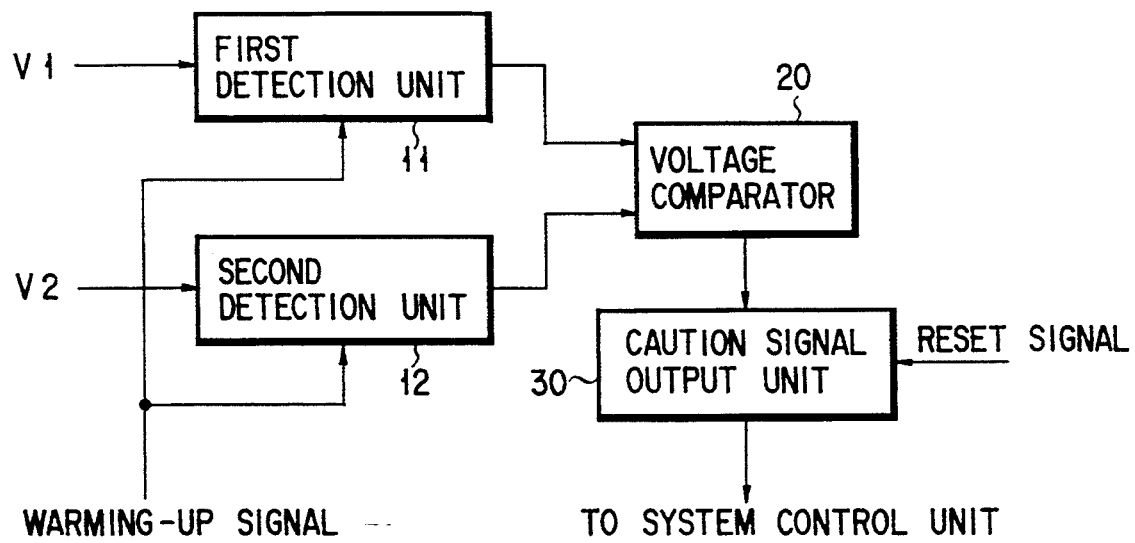
F I G. 7B

X-RAY COMPUTED TOMOGRAPHY APPARATUS

BACKGROUND OF THE INVENTION

1. Field of the Invention

The present invention relates to an X-ray computed tomography apparatus and, more particularly, to the functional maintenance of a slip ring system of an X-ray computed tomography apparatus.

2. Description of the Related Art

An X-ray computed tomography apparatus comprises a rotating frame section and fixed section, and radiates X-rays from an X-ray tube mounted on the rotating frame section onto a to-be-diagnosed object while rotating the rotating frame section, thus diagnosing the object.

Of such X-ray computed tomography apparatuses, an X-ray computed tomography apparatus having an X-ray generating system, e.g., an X-ray tube or a high-voltage generating device, mounted on a rotating frame section has recently become popular. In this apparatus having the X-ray generating system mounted on the rotating frame section, electric power is supplied to the X-ray generating system while a brush is brought into contact with a ring-like conductor, i.e., a slip ring, and their electrical coupling is maintained.

In the above-described apparatus, since the slip ring and the brush are mechanically in contact with each other, abrasion is caused on the slip ring and the brush upon rotation of the slip ring. The abrasion caused on the slip ring and the brush due to the contact with each other, and abrasion powder produced by the abrasion is a factor that increases the contact resistance between the slip ring and the brush. This increase in contact resistance causes a decrease in input voltage on the power-receiving member side, i.e., the X-ray generating system mounted on the rotating frame section, especially when electric power is transmitted through the slip ring and the brush. Therefore, an increase in contact resistance between the slip ring and the brush is a factor that degrades the performance of the X-ray computed tomography apparatus.

In order to compensate for the above-mentioned defect and maintain the high performance of the X-ray computed tomography apparatus, periodical maintenance is required. However, the performance of the X-ray computed tomography apparatus may not be satisfactorily maintained by performing only periodic maintenance, e.g., removal of abrasion powder by brushing the slip ring.

The reason why is that a contact resistance/abrasion is a phenomenon which is affected significantly by an operation environment, a frequency in use, etc.

As described above, since electric power is supplied to the X-ray generating unit or the like mounted on the rotating frame section by mechanically bringing the slip ring into contact with the brush, the high performance of the X-ray computed tomography apparatus cannot be maintained as sufficient electric power cannot be supplied to the rotating frame section with an increase in contact resistance between the slip ring and the brush.

SUMMARY OF THE INVENTION

It is an object of the present invention to detect a decrease in power supplied to an X-ray generating system mounted on a rotating frame section with an increase in contact resistance between a slip ring and a brush so as to predict maintenance time, thereby maintaining the high performance of an X-ray computed tomography apparatus.

An X-ray computed tomography apparatus of the present invention is characterized by comprising: a rotating frame section; an X-ray generating system, mounted on the rotating frame section, for generating X-rays; electric power transmission means, constituted by a slip ring and a brush, for supplying electric power to the X-ray generating system; and detection means for detecting an electric power supply state in the electric power transmission means.

More specifically, the detection means includes means for detecting a decrease in voltage in the X-ray generating system, means for detecting a change in voltage rise time in the X-ray generating system, or means for measuring a resistance between the slip spring and the brush.

In general, electric power supplied to the rotating frame section is gradually reduced with an increase in contact resistance due to the abrasion between the slip ring and the brush. Since the present invention includes means for detecting the state of supply of electric power to the slip ring and the brush, a predetermined signal indicating a reduction in electric power can be detected before the electric power supplied to the rotating frame section is reduced below predetermined electric power. According to the present invention, therefore, the necessity of maintenance can be displayed in response to a detection signal having a predetermined value before the performance of the X-ray computed tomography apparatus is degraded to a limit owing to a reduction in electric power supplied to the rotating frame section. In addition, abrasion powder can be removed by operating a self-cleaning function, if it is provided, e.g., brushing the slip ring. According to the present invention, deterioration in performance of the X-ray computed tomography apparatus is detected before desired performance cannot be obtained. Therefore, losses, e.g., incapability to operate the X-ray computed tomography apparatus in use, can be reduced.

In addition to warning the user, the above-mentioned detection signal may be stored as maintenance information or may be treated as information for centralized management for a remote-diagnosis system.

Furthermore, since insufficient X-ray irradiation owing to a reduction in power supplied to the rotating frame section can be detected in advance, retaking of an X-ray tomographic image due to insufficient X-ray irradiation can be prevented, thereby reducing an excessive dose of radiation on a patient.

According to the present invention, therefore, the reliability of the X-ray computed tomography apparatus can be improved.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 1 is a block diagram showing a circuit for detecting a signal for the functional maintenance of a slip ring system according to the first embodiment of the present invention;

FIG. 2 is a circuit diagram showing a measurement place for signal detection in FIG. 1;

FIG. 3 is a circuit diagram showing a circuit for detecting a signal for the functional maintenance of a slip ring system according to the second embodiment of the present invention;

FIG. 4 is a circuit diagram showing a measurement place for signal detection in FIG. 3;

FIGS. 5A and 5B are graphs for explaining an operation of the apparatus of the second embodiment;

FIGS. 6A and 6B are circuit diagrams showing circuits for detecting a signal for the functional maintenance of a slip ring system according to the third embodiment of the present invention; and FIGS. 7A and 7B are circuit diagrams showing circuits for detecting a signal for the functional maintenance of a slip ring system according to the fourth embodiment of the present invention.

DETAILED DESCRIPTION OF THE PREFERRED EMBODIMENTS

In general, an X-ray computed tomography apparatus comprises a rotating frame section and a fixed section, and radiates X-rays from an X-ray tube mounted on the rotating frame section onto a to-be-diagnosed object while rotating the rotating frame section, thus diagnosing the object.

According to the present invention, there is provided an X-ray computed tomography apparatus having an X-ray generating system, e.g., a high-voltage generating device, mounted on a rotating frame section, wherein when electric power is supplied to the X-ray generating system while a brush of a fixed section is brought into contact with a ring-like conductor, i.e., a slip ring mounted on the rotating frame section, and their electrical coupling is maintained, a reduction in the supplied electric power is detected.

In general, a reduction in electric power supplied to the X-ray generating system mounted on the rotating frame section, i.e., a reduction in electric power supplied (to be referred to as supplied electric power hereinafter) to the X-ray generating system mounted on the rotating frame section with an increase in contact resistance, appears as a decrease in output voltage from the X-ray generating system, a decrease in output current from the X-ray generating system, or a change in rise time characteristics of an output voltage from the X-ray generating system.

FIG. 1 is a block diagram showing a circuit for detecting a reduction in supplied power to perform functional maintenance of a slip ring system according to the first embodiment of the present invention. FIG. 2 is a schematic circuit diagram showing a place where a voltage is measured by using the detection circuit shown in FIG. 1.

In the first embodiment of the present invention, a place where a decrease in voltage supplied (to be referred to as a supplied voltage hereinafter) to the X-ray generating system with an increase in contact resistance between the slip ring and the brush is shown.

Referring to FIG. 2, which shows the measurement place, electric power is supplied from a power source 70 to an X-ray generating system 75 through a slip ring system 85 constituted by a slip ring and a brush. The slip ring system 85 has an internal resistance 80 (including a contact resistance).

Referring to FIGS. 1 and 2, this embodiment comprises a detection unit 10 for detecting a supplied voltage $V_d$ to the X-ray generating system 75 on a rotating frame section, a voltage comparator 20 for comparing the supplied voltage $V_d$ with a predetermined reference voltage $V_r$ and outputting a comparison output, and a caution signal output unit 30 for outputting a caution signal on the basis of the comparison output. This caution signal is input to a system control unit (not shown) on a fixed section. Therefore, a decrease in the supplied voltage $V_d$ can be checked by a user in advance through the system control unit.

The apparatus having the above-described arrangement will be described below.

When X-ray irradiation is started, the supplied voltage $V_d$ to the X-ray generating system 75 is input to the voltage comparator 20 through the detection unit 10. The voltage comparator 20 compares the input supplied voltage $V_d$ with the reference voltage $V_r$ and outputs a comparison output to the caution signal output unit 30 when the supplied voltage $V_d$ becomes lower than the reference voltage $V_r$, i.e., the supplied power is reduced. In this case, the reference voltage $V_r$ can be set to be 92% of a standard input voltage, if the input voltage allowable range of the X-ray generating system is ±10%. The reference voltage $V_r$ can be changed depending on the load condition for X-ray irradiation.

A voltage change amount $\Delta V_d = V_d - V_d'$ is measured from the supplied voltage $V_d$ to the X-ray generating system before X-ray irradiation and a supplied voltage $V_d'$ during X-ray irradiation. When the change amount $\Delta V_d$ exceeds the reference voltage $V_r$, a caution signal is output. In this case, since an input current I is substantially determined by an X-ray condition, if a limit of the resistance of the slip ring is represented by R, $V_r = IR$.

The caution signal output unit 30 outputs a caution signal to the system control unit (not shown) arranged on the fixed section in accordance with the comparison output, thus warning abnormality in the voltage supplied to the rotating frame section. The caution signal output unit 30 is constituted by a bistable pulse generator, e.g., a flip-flop. The caution signal output unit 30 keeps outputting the caution signal until a reset signal is input by the user. The caution signal output unit 30 may be constituted by a monostable pulse generator, e.g., a monostable multi-vibrator to keep outputting a caution signal for only a predetermined period of time or during only a period in which the abnormality in the supplied voltage $V_d$ continues.

As described above, according to the present invention, since the apparatus includes the means for detecting an increase in contact resistance between the slip ring and the brush by detecting a decrease in voltage supplied to the rotating frame section, a predetermined signal can be detected before the supplied voltage to the rotating frame section decreases below a reference value owing to an increase in contact resistance, generally caused by gradual abrasion between the slip ring and the brush. Therefore, before the performance of the X-ray computed tomography apparatus is degraded by a decrease in supplied voltage to the rotating frame section, the necessity of maintenance can be displayed in response to a predetermined detection signal, or a self-cleaning function, if it is provided, can be operated to, for example, remove abrasion powder by brushing the slip ring. Since degradation in performance of the X-ray computed tomography apparatus can be detected before required performance is lost, losses caused by the degradation in performance, e.g., incapability to operate the X-ray computed tomography apparatus in use, can be reduced.

In addition to warning the user, the above-mentioned detection signal may be stored as maintenance information or may be treated as information for centralized management for a remote-diagnosis system.

Furthermore, since insufficient X-ray irradiation owing to a reduction in power supplied to the rotating frame section can be detected in advance, retaking of an X-ray tomographic image due to insufficient X-ray irradiation can be prevented, thereby reducing an excessive dose of radiation on a patient.

With the above-described effects, the reliability of the X-ray computed tomography apparatus can be improved.

FIG. 3 is a circuit diagram showing a circuit for detecting a reduction in supplied power to perform functional maintenance of a slip ring system according to the second embodiment of the present invention. FIG. 4 is a circuit diagram showing a measurement place for signal detection in FIG. 3. The same reference numerals in the second embodiment shown in FIG. 3 and FIG. 4 denote the same parts as in the first embodiment, and a description thereof will be omitted. In FIG. 4, a measurement point of voltage is between X-ray tube 71 and high-voltage generating device 72.

A decrease in supplied voltage $V_d$ with an increase in the contact resistance between a slip ring and a brush leads to a reduction in maximum output of an X-ray generating system. This phenomenon appears as a change in time it takes for the output of an X-ray tube 71 to rise to a setting output voltage.

The second embodiment utilizes the above-described function and detects degradation in the function of a slip ring system by detecting a change in rise time of an output voltage $V_0$ to the X-ray tube in the X-ray generating system.

In addition to the circuit arrangement of the first embodiment, the circuit of the second embodiment has the following components arranged between the voltage comparator 20 and the caution signal output unit 30: a single pulse generator 40 for generating a pulse for a predetermined period of time after X-ray irradiation is started; a first AND circuit 50 for receiving an X-ray irradiating signal and an output signal from the voltage comparator 20 and outputting an AND signal of the two input signals; and a second AND circuit 60 for receiving an output from the first AND circuit 50 and an output from the single pulse generator 40 and outputting an AND signal of the two input signals.

An output voltage $V_0$ to an X-ray tube 71 is input to the voltage comparator 20 through a detection unit 10. The voltage comparator 20 compares the supplied voltage $V_0$ with a predetermined reference voltage $V_r$, and outputs a comparison output to one input terminal of the first AND circuit 50 if the supplied voltage $V_0$ is lower than the reference voltage $V_r$. An X-ray irradiating signal is continuously input to the other input terminal of the first AND circuit 50 during X-ray irradiation. The first AND circuit 50 logically ANDs the comparison signal and the X-ray irradiating signal and outputs the resultant data to one terminal of the first AND circuit 50. The X-ray irradiating signal is also input to the single pulse generator 40. The single pulse generator 40 generates a pulse of predetermined duration in accordance with a starting pulse of the X-ray irradiating signal. The pulse is output to the other terminal of the second AND circuit 60. The second AND circuit 60 logically ANDs the pulse and the output from the first AND circuit 50 and outputs the resultant data to the caution signal output unit 30.

An operation of the apparatus of the second embodiment, which has the above-described arrangement, will be described in detail below with reference to FIGS. 3, 5A, and 5B.

FIG. 5A is a graph showing a change in rise time characteristics of a voltage owing to degradation in a power supply system. FIG. 5B is a timing chart of outputs at the respective portions in the circuit shown in FIG. 3.

Referring to FIG. 5A, a curve A indicates a voltage rise time characteristic curve in a case wherein the power supply system is free from degradation; a curve B, a voltage rise time characteristic curve in a case wherein degradation in the power supply system can be allowed; and a curve C, a voltage rise time characteristic curve in a case wherein degradation in the power supply system cannot be allowed. The following description will be made on the assumption that the output of the single pulse generator 40 rises at X-ray irradiation start time $t_0$ and falls at time $t_2$ afterward. Referring to FIG. 5A, reference symbol Vs denotes a setting voltage; and $V_r$, a reference voltage (comparison voltage).

In FIG. 5A, when X-ray irradiation starts at time $t_0$, the voltages represented by the voltage rise time characteristics A, B, and C respectively rise depending on the degrees of degradation in the respective power supply systems, i.e., the contact resistances between the slip rings and the brushes. At this time, since terminals a and b are set at high level, a terminal c and a terminal d are set at high level and low level, respectively. As a result, a terminal e is kept at low level. At time $t_2$, the curve A reaches the reference voltage $V_r$. As indicated by the solid lines, since the terminals a and c is set at low level, the terminal e is kept at low level. With the curve A, therefore, no signal is output from the second AND circuit 60. Subsequently, with regard to the curve A, no changes appear at the output terminal, and hence a description thereof will be omitted. With regard to the curves B and C, the initial conditions of the output terminals are maintained at time $t_1$.

At time $t_2$, the curve B reaches the reference voltage $V_r$. In this case, the terminal d is set at high level, but the terminal c is set at low level. As a result, the terminal e is kept at low level, and hence no signal is output from the terminal e, as in the case of the curve A. Since the curve C has not reached the reference voltage $V_r$ yet, the terminal c is kept at high level, and the terminal d is set at high level. Consequently, with regard to the curve C, the terminal e is set at high level at time $t_2$, as indicated by the broken line, and a signal is kept output to the caution signal output unit 30 for the period of time indicated by the hatched portion. At time $t_3$, since the curve C reaches the reference voltage $V_r$, the terminal e is set at low level, and the output from the second AND circuit 60 is disabled.

The signal output from the terminal e of the caution signal output unit 30 is processed in the same manner as in the first embodiment.

As described above, in the second embodiment, since the supplied power to the rotating frame section can be decreased as in the first embodiment, the same effects as those of the first embodiment can be obtained.

As shown in FIG. 5A, if the voltage rise time is defined as the time it takes for the voltage to reach 90% of the setting voltage, i.e., $V_d$=(setting voltage)×0.9, and a pulse generated by the single pulse generator 40 is defined as (the allowable rise time of the apparatus)×0.9, a caution signal can be generated before the performance of the X-ray computed tomography apparatus degrades with a reduction in supplied power.

FIGS. 6A and 6B are circuit diagrams showing circuits for the functional maintenance of a slip ring system according to the third embodiment of the present invention. In this embodiment, degradation in the function of the slip ring system is detected by directly measuring the internal resistance of a slip ring.

FIG. 6A is a schematic circuit diagram showing the arrangement of an X-ray computed tomography apparatus having two or more brushes mounted therein for each slip ring channel. FIG. 6B is a circuit diagram showing an arrangement in which a resistance measuring means is arranged in the circuit shown in FIG. 6A. The embodiment can be applied to a case wherein two or more brushes are mounted for each slip ring channel.

Referring to FIG. 6A, the X-ray computed tomography apparatus includes a fixed section and a rotating frame section. A power source 70 and an X-ray generating system 75 are respectively arranged in the fixed section and the rotating frame section. The power source 70 of the fixed section and the X-ray generating system 75 of the rotating frame section are electrically connected to each other through a slip ring system 85. In this case, the slip ring system 85 has its own internal resistance 80 (contact resistance).

FIG. 6B shows a circuit obtained by adding a measurement device 90 for measuring resistance to the arrangement shown in FIG. 6A. With this arrangement, the contact resistance between the power source 70 and the measurement device 90 can be directly measured by switching between the power source 70 and the measurement device through a switching unit 95. Referring to FIG. 6B, the internal resistance 80 is kept connected to the measurement device 90 through the switching unit 95 except during supplying the electric power to the rotating frame section (X-ray generating system). The measurement device 90 is designed to measure the resistance between the brushes within the same channel through the switching unit 95.

In the above-described arrangement, when the power source for the X-ray computed tomography apparatus is to be started, the contact resistance between the slip ring and the brushes can be measured by directly measuring the resistance between arbitrary brushes within the same channel by using the circuit shown in FIG. 6B before power is supplied to the slip ring system 85.

The measurement data obtained in the above-described manner is supplied to a system control unit (not shown) to be compared with a predetermined resistance. In accordance with this comparison result, it can be detected whether the contact resistance between the slip ring and the brushes abnormally increases.

According to this embodiment, since an increase in contact resistance between slip ring and the brushes can be measured in advance, the same effects as those of the first and second embodiments can be obtained. Although the circuit of the third embodiment is more complicated than the circuits of the first and second embodiments, contact resistance can be measured from the fixed section instead of the rotating frame section, unlike the first and second embodiments. In addition, the resistance of a ground slip ring can also be measured unlike the first and second embodiments which are designed to measure contact resistance by measuring voltages.

FIGS. 7A and 7B are circuit diagrams showing circuits for detecting a signal for the functional maintenance of a slip ring system according to the fourth embodiment of the present invention. The first to third embodiments are designed to measure the contact resistance between the slip ring and the brush from the fixed section side or the rotating frame section side. In this embodiment, the contact resistance between a slip ring and a brush is measured when the apparatus comprises means for transferring signals detected between the rotating frame section and the fixed section. The same reference numerals in FIGS. 7A and 7B denote the same parts as in FIGS. 1 and 2, and a detailed description thereof will be omitted.

In the fourth embodiment, voltages respectively measured at the rotating frame section and the fixed section are compared with each other, and a caution signal is output when the voltage difference becomes lower than a predetermined value.

A detailed operation of the embodiment will be described below with reference to FIGS. 7A and 7B.

As shown in FIG. 7A, in the apparatus of the fourth embodiment, a voltage on the fixed section side (i.e., power source voltage $V_1$) is compared with a voltage on the rotating frame section side (i.e., a voltage $V_2$ of an X-ray generating system) while the rotating frame section is rotated. These voltages $V_1$ and $V_2$ are measured upon supplying a maximum current to the X-ray generating system mounted on the rotating frame section (i.e., upon performing test irradiation) during a warming-up period. This voltage measurement may be continuously performed during X-ray irradiation.

The voltages $V_1$ and $V_2$ measured in this manner are respectively input to a first detection unit 11 and a second detection unit 12, as shown in FIG. 7B. The voltages $V_1$ and $V_2$ detected by the first and second detection units 11 and 12 are input to a voltage comparator 20. The voltage comparator 20 calculates a voltage difference $\Delta V = V_1 - V_2$. When the voltage difference $\Delta V$ reaches, for example, $-1\%$, the voltage comparator 20 outputs a caution signal to a caution signal output unit 30. The subsequent operation is the same as that in the first embodiment.

With the above-described operation, degradation in supplied power to the rotating frame section can be measured similar to the first to third embodiments.

The present invention is not limited to the above-described embodiments.

In the above embodiments, a change in supplied power is detected by measuring a change in the supplied voltage $V_d$ and a change in contact resistance. However, a change in supplied power can also be detected by measuring a change in current supplied to the rotating frame section.

In addition, in the fourth embodiment, a change in contact resistance during rotation of the rotating frame section is measured by measuring a change in voltage.

However, as in the second embodiment, a change in contact resistance can be measured by measuring a change in voltage rise time.

Various changes and modifications can be made within the spirit and scope of the invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An X-ray computed tomography apparatus comprising:
   a rotating frame section;
   an X-ray generating system, mounted on said rotating frame section, for generating X rays;
   electric power transmission means, constituted by a slip ring and a brush, for supplying electric power to said X-ray generating system; and
   detection means for detecting a defect in said electric power transmission means.

2. An apparatus according to claim 1, further comprising cleaning means for performing a self-cleaning operation with respect to said slip ring on the basis of the electric power supply state detected by said detection means.

3. An apparatus according to claim 2, wherein said cleaning means includes means for brushing said slip ring.

4. An apparatus according to claim 1, wherein said detection means includes means for detecting a decrease in power in said X-ray generating system.

5. An apparatus according to claim 4, wherein said means for detecting the decrease in power includes
   voltage detection means for detecting a voltage of said X-ray generating system,
   voltage comparing means for comparing the voltage detected by said voltage detection means with a predetermined reference voltage and outputting a comparison output, and
   caution signal output means for outputting a caution signal on the basis of the comparison output.

6. An apparatus according to claim 5, wherein said voltage comparing means includes means for using a difference of voltage by load condition before and after X-ray irradiation.

7. An apparatus according to claim 5, wherein said caution signal output means includes one of a bistable pulse generator and a monostable pulse generator for generating a caution signal on the basis of the comparison output.

8. An apparatus according to claim 4, wherein said means for detecting the decrease in voltage includes
   first detection means for detecting a voltage of said X-ray generating system,
   second detection means for detecting an input voltage including a slip ring of a side-of supplying an electric power to said X-ray generating system,
   voltage comparing means for comparing the voltage detected by said first detection means with the voltage detected by said second detection means and outputting a comparison output, and
   caution signal output means for outputting a caution signal on the basis of the comparison output.

9. An apparatus according to claim 1, wherein said detection means includes means for detecting a change in voltage rise time in said X-ray generating system.

10. An apparatus according to claim 9, wherein said X-ray generating system outputs an X-ray irradiating signal when X-ray irradiation is started, and
    said means for detecting the change in voltage rise time includes
    voltage detection means for detecting a voltage of said X-ray generating system,
    voltage comparing means for comparing the voltage detected by said voltage detection means with a predetermined reference voltage and outputting a comparison output,
    monostable pulse generating means for generating a pulse for a predetermined period of time on the basis of the X-ray irradiating signal,
    a first AND circuit for ANDing the X-ray irradiating signal and an output from said monostable pulse generating means,
    a second AND circuit for ANDing an output from said first AND circuit and the pulse from said monostable pulse generating means, and
    caution signal output means for outputting a caution signal on the basis of an output from said second AND circuit.

11. An apparatus according to claim 1, wherein said detection means includes means for measuring a resistance between said slip ring and said brush.

12. An apparatus according to claim 1, wherein said X-ray generating system includes an X-ray tube for generating the X-rays.

13. An apparatus according to claim 12, wherein said X-ray generating system includes an X-ray high-voltage unit for applying a high voltage to said X-ray tube to generate X-rays.

14. An X-ray computed tomography apparatus comprising:
    a rotating frame section;
    an X-ray generating system, mounted on said rotating frame section, for generating X rays;
    electric power transmission means, constituted by a slip ring and a brush, for supplying electric power to said X-ray generating system; and
    detection means for detecting a change in voltage rise time in said X-ray generating system so as to detect a defect of said electric power transmission means.

15. An apparatus according to claim 14, further comprising cleaning means for performing a self-cleaning operation with respect to said slip ring on the basis of the electric power supply state detected by said detection means.

16. An apparatus according to claim 15, wherein said cleaning means includes means for brushing said slip ring.

* * * * *